(12) United States Patent
Thiel et al.

(10) Patent No.: US 7,351,310 B2
(45) Date of Patent: Apr. 1, 2008

(54) RECTIFICATIVE SEPARATION OF FLUIDS COMPRISING (METH) ACRYLIC MONOMERS

(75) Inventors: Joachim Thiel, Neustadt (DE); Albrecht Dams, Wachenheim (DE); Juergen Schroeder, Ludwigshafen (DE)

(73) Assignee: BASF Aktiengesellschaft, Ludwigshafen (DE)

(*) Notice: Subject to any disclaimer, the term of this patent is extended or adjusted under 35 U.S.C. 154(b) by 285 days.

(21) Appl. No.: 10/658,257

(22) Filed: Sep. 10, 2003

(65) Prior Publication Data

US 2004/0129021 A1 Jul. 8, 2004

(30) Foreign Application Priority Data

Jan. 8, 2003 (DE) ................. 103 00 499

(51) Int. Cl.
*B01D 3/34* (2006.01)
*B01D 5/00* (2006.01)
*C07C 51/42* (2006.01)

(52) U.S. Cl. ............ 203/8; 62/120; 62/617; 202/158; 202/185.2; 202/186; 203/9; 203/49; 203/87; 203/DIG. 21; 562/600

(58) Field of Classification Search ........... 203/8, 203/9, 49, 87, DIG. 21; 62/119, 120, 617; 202/158, 185.2, 186; 562/600
See application file for complete search history.

(56) References Cited

U.S. PATENT DOCUMENTS

| | | | |
|---|---|---|---|
| 4,188,793 A * | 2/1980 | Watson et al. ........... 62/48.2 |
| 4,333,917 A * | 6/1982 | Dorr et al. .............. 423/522 |
| 4,986,884 A * | 1/1991 | Arlt et al. ................. 203/8 |
| 5,078,758 A * | 1/1992 | Maller et al. ............. 95/211 |
| 5,578,173 A * | 11/1996 | Toot et al. ................ 203/6 |
| 6,257,018 B1 * | 7/2001 | Kelly et al. .............. 62/617 |
| 6,372,944 B1 * | 4/2002 | Matsumoto et al. ...... 562/600 |
| 6,409,886 B1 * | 6/2002 | Matsumoto et al. ......... 203/8 |
| 6,423,875 B1 * | 7/2002 | Machhammer et al. .... 568/476 |
| 6,596,129 B1 * | 7/2003 | Yoneda et al. ............. 203/2 |

(Continued)

FOREIGN PATENT DOCUMENTS

DE 101 15 277 6/2002

(Continued)

OTHER PUBLICATIONS

Derwent Publications, AN 2001-293790, XP-002277806, JP 2000-344688, Dec. 12, 2000.

*Primary Examiner*—Virginia Manoharan
(74) *Attorney, Agent, or Firm*—Oblon, Spivak, McClelland, Maier & Neustadt, P.C.

(57) ABSTRACT

A process for rectificatively separating fluids including (meth)acrylic monomers in a rectification column by directly cooling the vapor including (meth)acrylic monomers rising to the top of the rectification column to form top condensate including (meth)acrylic monomers, the condensation space at the top of the column being separated from the region of the rectification column containing the separating internals only by at least one chimney tray from which the top condensate formed is removed from the rectification column, which includes effecting the direct cooling of the vapor in the condensation space in at least two spray zones which are spatially successive and are flowed through by vapor by spraying supercooled top condensate including added polymerization inhibitor, and the temperature of the sprayed supercooled top condensate becoming lower from spray zone to spray zone in the flown direction of the vapor.

14 Claims, 3 Drawing Sheets

U.S. PATENT DOCUMENTS

| | | | |
|---|---|---|---|
| 6,676,808 B2* | 1/2004 | Hamamoto et al. | 203/8 |
| 6,679,939 B1* | 1/2004 | Thiel et al. | 95/210 |
| 6,727,383 B1* | 4/2004 | Nestler et al. | 562/600 |
| 2004/0046270 A1* | 3/2004 | Diehl et al. | 261/78.2 |

FOREIGN PATENT DOCUMENTS

| | | |
|---|---|---|
| EP | 1 044 957 | 10/2000 |
| EP | 1 097 742 | 5/2001 |

* cited by examiner

RECTIFICATIVE SEPARATION OF FLUIDS COMPRISING (METH) ACRYLIC MONOMERS

The present invention relates to a process for rectificatively separating fluids comprising (meth)acrylic monomers in a rectification column by directly cooling the vapor comprising (meth)acrylic monomers rising to the top of the rectification column to form top condensate comprising (meth)acrylic monomers, the condensation space at the top of the column being separated from the region of the rectification column containing the separating internals only by at least one chimney tray from which the top condensate formed is removed from the rectification column.

In this document, the notation "(meth)acrylic monomers" is an abbreviation for "acrylic monomers and/or methacrylic monomers".

In this document, the term "acrylic monomers" is an abbreviation for "acrolein, acrylic acid and/or esters of acrylic acid".

In this document, the term "methacrylic monomers" is an abbreviation for "methacrolein, methacrylic acid and/or esters of methacrylic acid".

In particular, (meth)acrylic monomers addressed in this document are intended to include the following (meth) acrylic esters: hydroxyethyl acrylate, hydroxyethyl methacrylate, hydroxypropyl acrylate, hydroxypropyl methacrylate, glycidyl acrylate, glycidyl methacrylate, methyl acrylate, methyl methacrylate, n-butyl acrylate, isobutyl acrylate, isobutyl methacrylate, n-butyl methacrylate, tert-butyl acrylate, tert-butyl methacrylate, ethyl acrylate, ethyl methacrylate, 2-ethylhexyl acrylate, 2-ethylhexyl methacrylate, N,N-dimethylaminoethyl acrylate and N,N-dimethylaminoethyl methacrylate.

(Meth)acrylic monomers are important starting compounds for preparing polymers which find use, for example, as adhesives.

(Meth)acrolein and (meth)acrylic acid are prepared on the industrial scale predominantly by catalytic gas phase oxidation of suitable $C_3/C_4$ precursor compounds (or of precursor compounds of these precursor compounds), in particular of propene and propane in the case of acrolein and acrylic acid and of isobutene and isobutane in the case of methacrylic acid and methacrolein. However, also suitable are starting materials in addition to propene, propane, isobutene and isobutane are other compounds containing 3 or 4 carbon atoms, for example isobutanol, n-propanol or the methyl ether of isobutanol (as a $C_4$ precursor). (Meth)acrylic acid can also be obtained from (meth)acrolein.

This normally results in a product gas mixture from which the (meth)acrylic acid and/or the (meth)acrolein have to be removed.

This removal is generally carried out in such a way that the (meth)acrylic acid and/or the (meth)acrolein are initially removed in a basic manner by absorption in a solvent (for example water or an organic solvent) or by fractional condensation of the product gas mixture, and the resulting condensate or absorbate is subsequently separated rectificatively (generally in a plurality of stages) to obtain more or less pure (meth)acrylic acid and/or (meth)acrolein (cf., for example, EP-A 717019, EP-A 1125912, EP-A 982289, EP-A 982287, DE-A 19606877, DE-A 1011527, DE-A 10224341 and DE-A 10218419). In this document, the fractional condensation addressed above should be regarded as falling under the definition of rectification. It differs from conventional rectification merely in that the mixture to be separated is fed in gaseous form (i.e. fully converted to vapor form) to the separating column (the rectification column). The term fluids used in this document is therefore intended to include both liquids and gas mixtures.

Esters of (meth)acrylic acid are obtainable, for example, by direct reaction of (meth)acrylic acid and/or (meth)acrolein with the appropriate alcohols. However, in this case also, product gas mixtures are initially obtained, from which the (meth)acrylic esters have to be removed, for example rectificatively.

The fluids or liquids which have been addressed above, comprise (meth)acrylic monomers and are to be processed rectificatively may contain the (meth)acrylic monomers either in more or less pure form or in solution.

The solution may either be aqueous or be an organic solvent. The specific type of the solvent is substantially insignificant to the process according to the invention. The content of (meth)acrylic monomers may be $\geq 2\%$ by weight, or $\geq 5\%$ by weight, or $\geq 10\%$ by weight, or $\geq 20\%$ by weight, or $\geq 40\%$ by weight, or $\geq 60\%$ by weight, or $\geq 80\%$ by weight, or $\geq 90\%$ by weight, or $\geq 95\%$ by weight, or $\geq 99\%$ by weight.

Depending on their composition, the fluids or liquids described which comprise (meth)acrylic monomers can be rectificatively separated either by the accumulation of the (meth)acrylic monomers at the top of the rectification column or by the accumulation of the (meth)acrylic monomers at the bottom of the rectification column. It will be appreciated that the fractions comprising the enriched (meth) acrylic monomers can also be withdrawn in the upper, lower or middle section of the rectification column.

In substantially all of the abovementioned cases, it is necessary to cool vapor which comprises more or less (meth)acrylic monomers and rises toward the top of the rectification column to form top condensate comprising (meth)acrylic monomers. The aforesaid is especially true when the rectificative separating process is conducted in such a way that the (meth)acrylic monomers accumulate at the top of the rectification column.

This is problematic in that (meth)acrylic monomers in condensed phase exhibit an increased tendency to undesired polymerization. As a consequence of this fact, the occurrence in rectification columns of condensate which comprises (meth)acrylic monomers and is free of polymerization inhibitor is to be avoided.

Therefore, DE-A 2027655, for example, recommends for this problem area the constant wetting of critical components of the rectification column with polymerization-inhibited reflux. Correspondingly, EP-A 1044957 describes specific nozzles whose components can be used to spray a rectification column with polymerization inhibitor-containing solution. In contrast, a solution to the problem recommended by DE-A 2246480 is to superheat critical column components, in order to prevent the formation of uninhibited condensate thereon (since polymerization inhibitors are generally involatile, the vapor phase within a rectification column is normally substantially free of polymerization inhibitor; condensate formation on column components from such vapor phase therefore naturally leads to condensate free of polymerization inhibitor whose (meth)acrylic monomers exhibit an increased tendency to polymerize).

A disadvantage of the proposed solution of DE-A 2246480 is that it cannot be used for the purpose of vapor cooling.

EP-A 1034824 recommends carrying out the relevant vapor cooling outside the rectification column by means of a tube bundle heat exchanger (external vapor cooling).

A disadvantage of this solution variant is, that it requires a gas-side connection from the top of the column to heat exchanger. Such a vapor pipe generally has a considerable length, since the heat exchanger is normally disposed on the ground for structural reasons. This results in the need to reliably suppress undesired polymerization also in the vapor pipe. To this end, the vapor pipe is advantageously trace-heated, in order to very substantially rule out condensate formation in the vapor pipe. A further disadvantage of the variant according to EP-A 1034824 then arises when the vapor rising to the top of the rectificiation column, in addition to (meth)acrylic monomers, additionally comprises constituents which condense only at extremely low temperatures, if at all, and leave the condensation region as offgas.

This is the case, for example, when the rectification column is flowed through by a molecular oxygen-containing gas (for example by air), in order to utilize the polymerization-inhibiting action of molecular oxygen. However, it is also the case when, for example, a fractional condensation of product gas of a heterogeneously catalyzed gas phase partial oxidation of $C_3/C_4$ compounds is carried out in the rectification column (for example according to DE-A 19924532 or according to DE-A 10247240). In these cases, it is necessary to keep the proportion of condensable constituents in the offgas very low (for example for reasons of an increased yield or for environmental reasons). A sharp separation of offgas and condensable constituents requires a particularly low operating temperature, if it is carried out by means of an indirect heat exchanger (for example a tube bundle heat exchanger).

EP-A 1097742 likewise recommends external cooling of the relevant vapors. It proposes either indirect cooling (for example by means of a tube bundle heat exchanger) or by direct cooling (for example by jetting in supercooled condensate) in a cooling apparatus spatially separated from the rectification column. For the purpose of separating offgas and constituents to be condensed (for example the (meth) acrylic monomers), EP-A 1097742 recommends the downstream connection of a separate aftercooler. A disadvantage of the recommendation of EP-A 1097742 is likewise the necessity of a connecting vapor pipe and the need for additional apparatus in the form of the aftercooler.

JP-A 2000/344688 teaches the implementation of the relevant vapor cooling by means of an indirect heat exchanger integrated into the top of the rectification column. Although a vapor pipe is then no longer needed, a disadvantage of this procedure is that the heat exchanger surface has to be continuously sprayed with polymerization inhibitor-containing condensate. In addition, the indirectness of the cooling in this case also entails particularly low operating temperatures for a sharp offgas separation, which is energetically disadvantageous.

DE-A 10220494 and DE-A 10200583 disclose, inter alia, the integration of the relevant vapor cooling into the top of the rectification column by the use of direct cooling. According to DE-A 10200583, condensate formed beforehand which has been supercooled and admixed with polymerization inhibitor is fed to the top region. A disadvantage of the teaching of DE-A 10200583 is that there are no further details on the specific configuration of such direct cooling.

According to the example of DE-A 10220494, the vapor condensation integrated into the top of the column is effected by means of two direct cooling circuits (quench circuits) connected in series. The first is operated by means of supercooled top condensate which has been condensed beforehand and admixed with polymerization inhibitor (in this document, supercooled in the given context always means that the top condensate, after its withdrawal from the rectification column, has been brought to a temperature lower than the withdrawal temperature before it is fed into the rectification column for the purpose of direct cooling) and the second by means of cooled water. A disadvantage of the procedure of DE-A 10220494 is that it uses two different coolants and the aqueous condensate resulting from the aqueous direct cooling, including the components of value contained therein, is disposed of (for example in a water treatment plant). The same applies to DE-A 10256147 as was stated with regard to DE-A 10220494.

Figure 1:
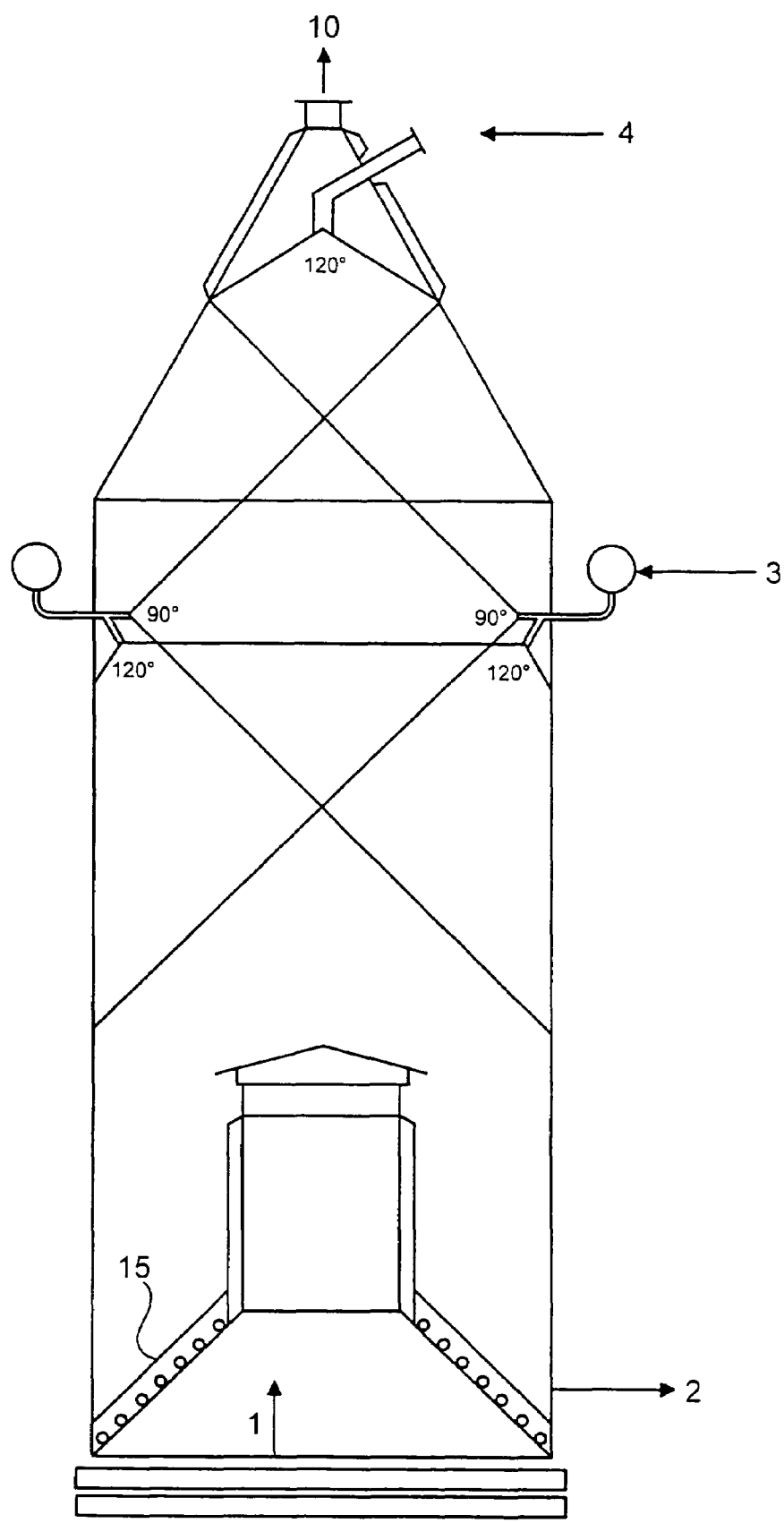
FIG. 1 is a schematic showing a rectification column of exemplary embodiments of the invention.

It is an object of the present invention to provide an improved process for rectificatively separating fluids comprising (meth)acrylic monomers in a rectification column by directly cooling the vapor comprising (meth)acrylic monomers rising to the top of the rectification column to form top condensate comprising (meth)acrylic monomers, the condensation space at the top of the column being separated from the region of the rectification column containing the separating internals only by at least one chimney tray from which the top condensate formed is removed from the rectification column.

We have found that this object is achieved by a process for rectificatively separating fluids comprising (meth)acrylic monomers in a rectification column by directly cooling the vapor comprising (meth)acrylic monomers rising to the top of the rectification column to form top condensate comprising (meth)acrylic monomers, the condensation space at the top of the column being separated from the region of the rectification column containing the separating internals only by at least one chimney tray from which the top condensate formed is removed from the rectification column, which comprises effecting the direct cooling of the vapor in the condensation space in at least two spray zones, which are spatially successive and are flowed through by vapour, by spraying supercooled top condensate comprising added polymerization inhibitor, and the temperature of the sprayed supercooled top condensate becoming lower from spray zone to spray zone in the flow direction of the vapor.

The advantage of the process according to the invention is based on the fact that firstly no vapor pipe is required, the condensate automatically occurs in polymerization-inhibited form, and secondly that the separation of offgas can be carried out sharply, in an energetically comparatively favorable manner.

For the section which contains the separating internals of the rectification column to be used in accordance with the invention, all common types come into consideration. In other words, the rectification column may be, for example, a tray column or a column having random packing or structured packing. It will be appreciated that the aforementioned internals may also be used in mixed form.

The random packings used may be, for example, rings, helices, saddles, Raschig, Intos or Pall rings, barrel or Intalox saddles, Top-Pak or braids.

Useful separating internals include, for example, bubble-cap trays, sieve trays, valve trays, tunnel-cap trays, Thormann trays and/or dual-flow trays. In particular, the process according to the invention is applicable in the case of rectification columns which contain exclusively dual-flow trays as separating internals (cf., for example, DE-A 10156988, EP-A 1029573 and DE-A 10230219).

However, it is also applicable in the case of rectification columns and processes whose separating section is configured according to DE-A 10243625 or according to DE-A 10247240 and whose process is carried out as described in these documents.

It is essential to the invention that the condensation space in the process according to the invention is attached directly to the section of the rectification column which contains the separating internals, and is separated from it only by at least one chimney tray. Preference is given in accordance with the invention to both spaces being separated only by one chimney tray.

On the chimney side, the at least one chimney tray leads into the condensation space. In its simplest embodiment, this is an empty pipe (i.e. a space-substantially free of internals) which is equipped zone by zone with spray nozzles. The diameter of the empty pipe may be greater or less than that of the chimney tray. At the connection point, it preferably has the same diameter as the chimney tray. More preferably, the empty pipe narrows conically in the upper section to the diameter of the offgas outlet (cf. FIG. 1). On the industrial scale, the largest diameter of the empty pipe may be from 0.5 to 5 m, frequently from 1 to 3 m. On the industrial scale, the height of the empty pipe is typically from 1 to 6 m, frequently from 2 to 4 m. The spray nozzles of a spray zone are normally arranged annularly in the empty pipe and are preferably supplied with the liquid to be sprayed via a common ring line. On the industrial scale, the number of spray nozzles per ring line is typically from 5 to 50, frequently from 10 to 30.

According to the invention, the spray cones of a spray zone preferably overlap horizontally and vertically (cf. FIG. 1), so that the entire volume can be homogeneously charged with spray droplets.

According to the invention, at least two ring lines arranged one on top of the other and having spray nozzles are required, and the temperature of the liquid to be sprayed decreases within the ring lines from bottom to top. In this case, it is advantageous when the spray cones of the different subsequent temperature ranges only touch and do not overlap. The latter requires an increased condensation efficiency and a sharper separation of offgas (10). Overlapping would accordingly be disadvantageous. In a particular embodiment of the process according to the invention, a last spray nozzle is disposed immediately below the offgas line (cf. FIG. 1), when there is a need for such an offgas line.

According to the invention, the atomizer nozzles may, for example, be those as described in DE-A 19924533. The liquid to be sprayed can be fed to such nozzles under pressure. The liquid to be sprayed can be atomized by decompressing it once it has attained a certain minimum flow rate in the nozzle bore. For the inventive purpose, it is also possible to use one-material nozzles, for example swirl chambers (full cone nozzles) (for example from Düsen-Schlick GmbH, DE, or from Sprayring Systems Deutschland GmbH).

According to the invention, preference is given to the spray nozzles being full cone spray nozzles having an opening angle of the spray cone in the range from 60° to 180°, preferably from 90° to 120°. According to the invention, the droplet diameter which is obtained on spraying is advantageously $\leq 1000$ μm. On the industrial scale, the throughput per spray nozzle in the spray zones disposed further down is typically from 1 to 50 m³/h, frequently from 5 to 20 m³/h. In the spray zones disposed further up, this amount is advantageously from 0.1 to 10 m³/h, frequently from 0.5 to 5 m³/h. On the industrial scale, the average length of flight of the droplets (until they collide with the wall) in the lower spray zones is typically from 0.5 to 10 m, frequently from 1 to 5 m. On the industrial scale, the average length of flight in the spray zones disposed further up are typically from 0.05 to 1 m, frequently from 0.1 to 0.5 m.

According to the invention, the surface of the condensation space above the spray region of the last spray zone and any existing offgas outlet may advantageously be trace-heated (5). The wall temperature should be from 5 to 10° C. above the temperature of the offgas when it leaves the last spray zone.

It is usually advantageous from an application point of view to use from 2 to 3 spray zones.

The condensate resulting from the direct cooling is collected on the chimney tray and removed from this, for example, via a nozzle by means of a pump.

The condensate (2) withdrawn from the chimney tray is partly recycled as reflux (6) into the section of the rectification column which contains the separating internals, partly used as feeds for the spray nozzles (after passing through indirect heat exchangers (7), (8) for the purpose of supercooling and addition of polymerization inhibitor (advantageously dissolved in the condensate (9))) and partly discharged as products or by-products (12).

From an application point of view, the diameter of the chimney tray advantageously corresponds to the diameter of the separating section of the rectification column. However, it may also be from 30% to 120%, or from 50% to 100% thereof.

Typical chimney tray diameters on the industrial scale are from 0.5 to 5 m, frequently from 1 to 3 m.

In the case of a chimney tray having only one chimney, this is generally disposed in the middle of the chimney tray. In addition, it advantageously has a slope (on all sides) from the chimney to the empty pipe (column) internal wall (this minimizes the amount of condensate running onto the chimney tray and reduces the delay time on the tray). The annular gap formed as a result is at the same time the pump reservoir (cf. FIG. 1 and FIG. 2).

When the chimney tray has a plurality of chimneys, a chimney arrangement and a slope of the chimney tray as described in DE-A 10159825 is advantageous. A hood on the particular chimney prevents condensate from getting through the chimney into the lower section of the rectification column containing the separating internals. According to the invention, the hoods are preferably as described in DE-A 10159825.

The diameter of a chimney is generally $\geq 10\%$ and $\leq 70\%$ of the chimney tray diameter. The aforementioned percentage is frequently in the range $\geq 25\%$ and $\leq 50\%$. In the case of industrial use, typical diameter values are from 0.2 to 1.5 m, frequently from 0.5 to 1.0 m, at chimney heights of from 1 to 3 m, or from 1.5 to 2.5 m.

According to the invention, preference is given to both the chimneys and the chimney tray being configured with thermal isolation against the separating section of the rectification column, in order to prevent or reduce uncontrolled condensation on the side facing the separating section. In the simplest manner, they have a double-walled design for this purpose. According to the invention, preference is given to applying trace heating (for example tubes or hoses ((15) in FIG. 1) flowed through by a heat carrier) to the upper surface of the lower of the two walls of the chimney tray (annular gap).

Preference is given to switching on this trace heating only after commencement of the rectification.

As already mentioned, the feed to the spray nozzles is supercooled by means of indirect heat exchangers. To this end, it is possible to use a plurality of heat exchangers connected in series or parallel. Typically, supercooling is effected to from 5 to 25° C. below the withdrawal temperature from the chimney tray. When the condensate consists of more than 90% by weight of (meth)acrylic monomers, the coolant used in the heat exchangers is at least partly, for example, river water. It is advantageous to insert a secondary cooling circuit. This prevents product exit into the cooling water in the event of leaks into the heat exchanger.

In the case of a rectification removal via the top of acrylic acid or methacrylic acid having an acid content of ≧90% by weight in the condensate and polymerization inhibition solely by means of hydroquinone monomethyl ether (MEHQ), and also air optionally flowing through, outlet temperatures of the condensate of ≧40° C. are to be avoided. The content of MEHQ in the condensate is advantageously from 50 to 250 ppm by weight.

According to the invention, the entire amount of spray condensate used, after its withdrawal from the chimney tray, is advantageously initially conducted via a first indirect heat exchanger (preferably operated with river water). Of this, a first portion (3) is fed to the first spray zone and the remainder to a second indirect heat exchanger (preferably operated with cooling sols) for the purpose of further cooling, before it is passed on completely (4) or partly to the second spray zone, etc. (cf. FIG. 2).

Figure 3:
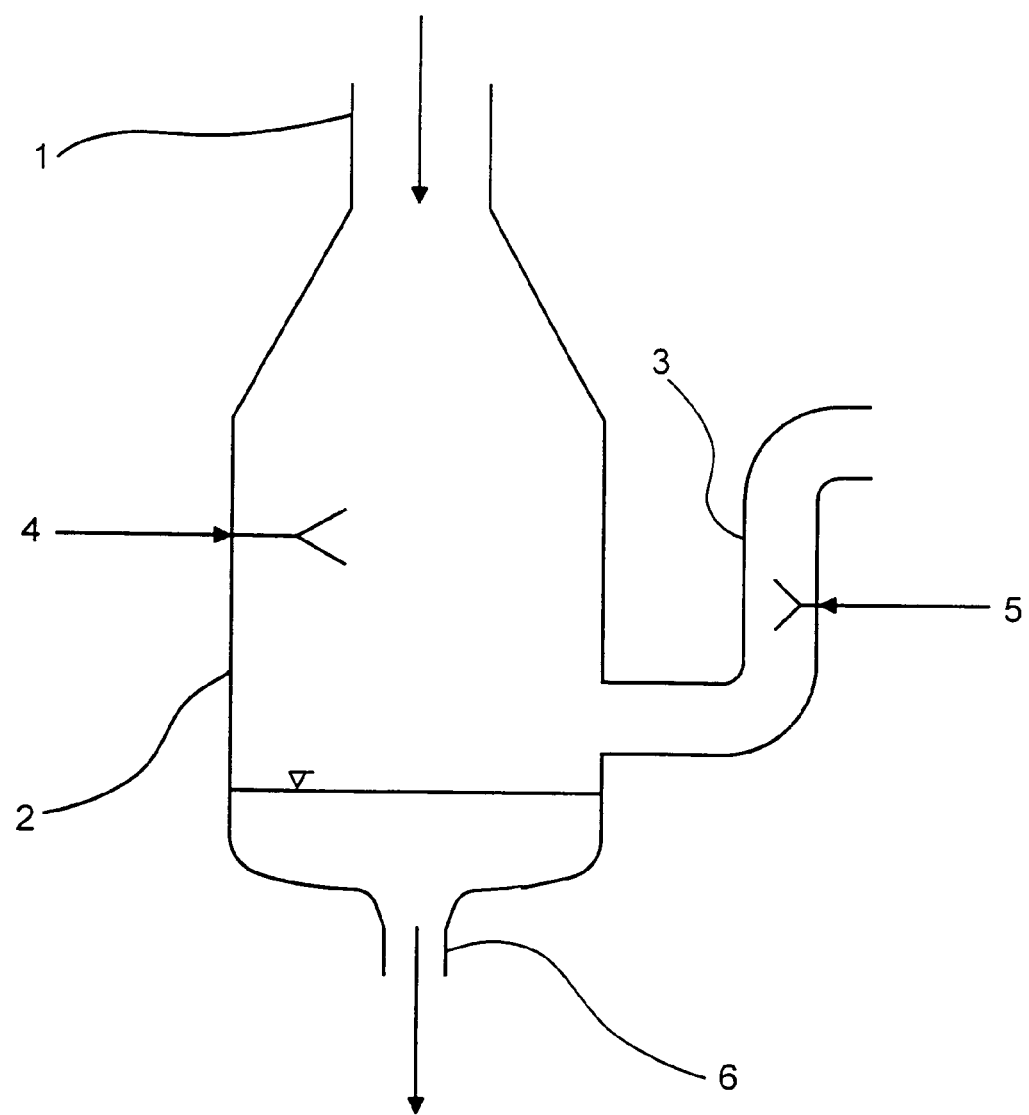
FIG. 3 is a schematic showing condensation space according to exemplary embodiments.

In an alternative embodiment, the condensation space may also be configured as in FIG. 3.

The vapor to be cooled is conducted via a vapor pipe (1) into the condensation space which consists of a main space (2) and a side arm (3).

Both in the main space and in the side arm, there is disposed a ring line having spray nozzles ((4) and (5) respectively).

The temperature $T_2$ of the feed to the spray nozzles (5) is lower than the temperature $T_1$ of the feed to the spray nozzles (4).

The condensate is removed via the line (6). A portion of it is discharged as the product, a portion used as reflux for the rectification column, and a portion fed in cooled form to the spray nozzles (4) and (5) after passing through the appropriate indirect heat exchanger.

The process according to the invention is applicable in the case of all (meth)acrylic monomers mentioned at the outset of this document.

It is applicable in particular in the case of a rectificative removal of acrylic acid from acrylic acid-containing mixtures, as described in EP-A 717029, EP-A 839790, U.S. Pat. No. 5,482,597, EP-A 713854, DE-A 19634614, U.S. Pat. No. 5,710,329, EP-A 1110940, DE-A 19853064, DE-A 4201697, DE-A 3641996, EP-A 1033359, DE-A 10138150, DE-A 10138101 and EP-A 648732. The same applies to the process of EP-A 648732, of EP-A 713854, of U.S. Pat. No. 5,482,597, of EP-A 839790, of DE-A 1980962 and of DE-A 4335172.

Figure 2:
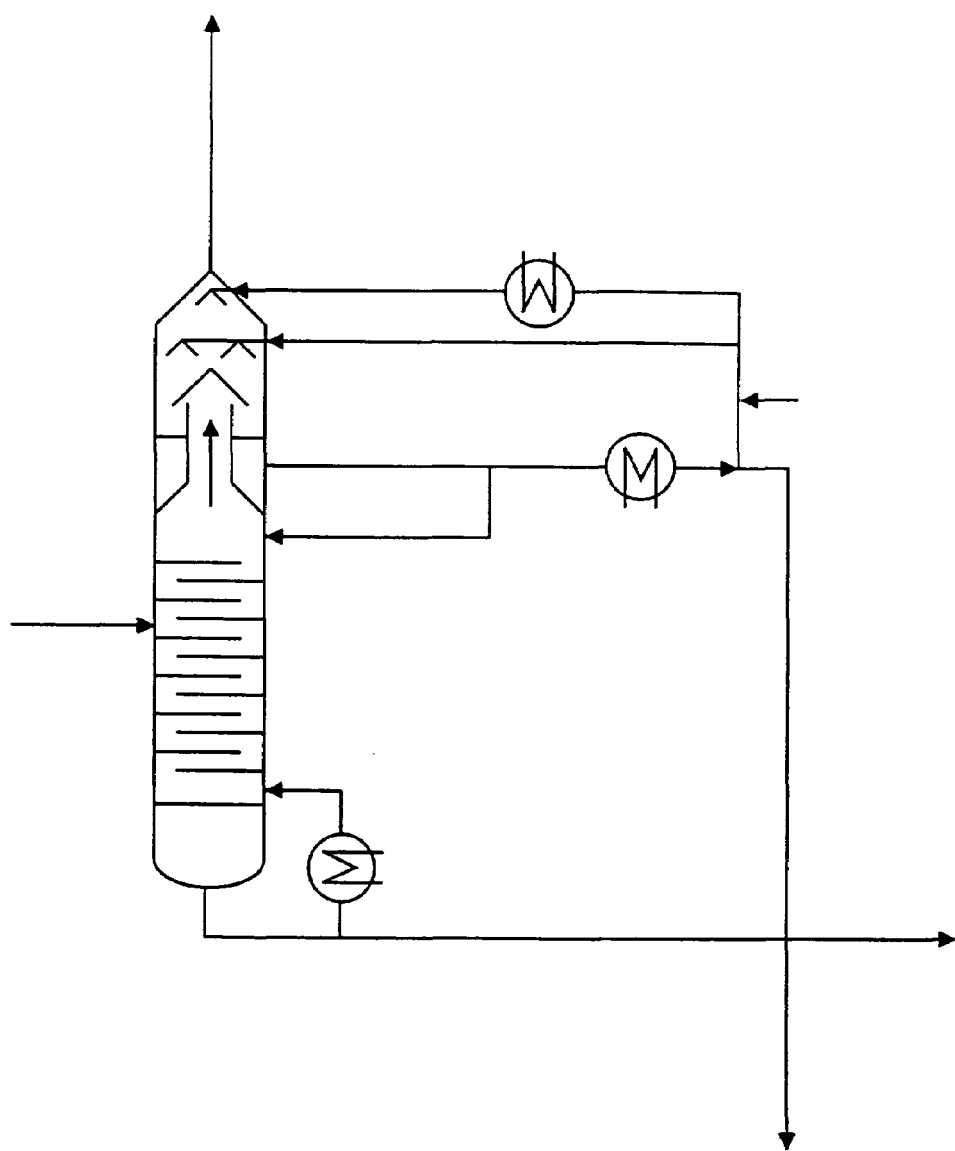
FIG. 2 is a schematic showing a pump reservoir according to exemplary embodiments of the invention.

All the numerical addresses used in this document relate to FIGS. 1 and 2. (11) means the mixture to be separated, (13) means withdrawn bottom liquid which is recycled after indirect heating into the lower section of the rectification column and (14) means discharged high boilers which are generally fed to thermal dissociation.

The content of (meth)acrylic monomers of the fluid mixtures comprising (meth)acrylic monomers to be separated in accordance with the invention may have the values mentioned at the outset of this document.

Useful polymerization inhibitors are all those disclosed by the prior art. Typical representatives of such polymerization inhibitors are phenothiazine, 4-methoxyphenol and 4-hydroxy-2,2,6,6-tetramethylpiperidine N-oxyl.

The specific temperatures to be used for the particular spray zones can be determined by those skilled in the art for the particular specific separating problem with the aid of a few experiments. In general, the top condensate to be sprayed in the process according to the invention will be sprayed with excess inhibition, so that the resulting new top condensate contains polymerization inhibitor to a sufficient extent.

Finally, the advantages of the process according to the invention will be summarized once again. The process according to the invention requires no vapor pipe connecting the separating unit and the condensation unit. The heat of condensation present in the condensate obtained can generally be removed at a comparatively high temperature in a first indirect heat exchanger, so that the heat exchanger for the purpose of supercooling the condensate can usually be operated using river water (the withdrawal stream 12 can also be branched off into the heat exchanger upstream of the entry of the condensate withdrawn). The use of successive spray zones results in a sharp condensative separation of offgas. The throughput required for this purpose of condensate to be sprayed in the higher spray zones is comparatively low. This is advantageous in that the condensate sprayed in them is usually subjected to a second cooling in heat exchangers operated with cooling sols to attain the low cooling temperatures. The requirement for sols is in this regard comparatively low. Overall, the condensation unit according to the invention can therefore be operated in an energetically favorable manner.

The implementation of the process according to the invention requires merely a rectification column comprising a section which contains separating internals and is completed at the top by at least one chimney tray and is continued into a spray condenser having at least two spray zones. The spray condenser is connected to the appropriate number of heat exchangers.

We claim:

1. A process for rectificatively separating fluids comprising (meth)acrylic monomers in a rectification column by directly cooling the vapor comprising:

forming a top condensate including (meth)acrylic monomers by allowing the (meth)acrylic monomers to rise to the top of the rectification column;

separating a condensation space at the top of the column from the region of the rectification column containing a separating internals only by at least one chimney tray which has at least one chimney, from which the top condensate formed is removed from the rectification column, effecting the direct cooling of the vapor in the condensation space in at least two spray zones, which are spatially successive and are flown through by vapor, by spraying in each of the at least two spray zones supercooled top condensate including added polymerization inhibitor through spray nozzles; and lowering a temperature of the sprayed supercooled top condensate from spray zone to spray zone in the flow direction of the vapor.

2. A process as claimed in claim 1, wherein at least one of the at least two spray zones is supplied via annularly mounted spray nozzles.

3. A process as claimed in claim 1, wherein the spray nozzles are full cone spray nozzles whose opening angle is from 60° to 180°.

4. A process as claimed in claim 3, wherein the opening angle is from 90° to 120°.

5. A process as claimed in claim 3, wherein the spray cones overlap one and the same spray zone.

6. A process as claimed in claim 3, wherein the spray cones of spatially successive spray zones do not overlap.

7. A process as claimed in claim 3, wherein the spray cones of spatially successive spray zones just touch.

8. A process as claimed in claim 1, wherein the rectification column is flowed through by a molecular oxygen-containing gas.

9. A process as claimed in claim 1, wherein the condensation space has an offgas outlet.

10. A process as claimed in claim 9, wherein the condensation space is an empty pipe which narrows conically toward the offgas outlet.

11. A process as claimed in claim 1, wherein the at least one chimney tray, from which the top condensate formed is removed from the rectification column, has a slope on all sides toward the inner wall of the condensation space.

12. A process as claimed in claim 1, wherein the at least one chimney tray, from which the top condensate formed is removed from the rectification column, and its at least one chimney, are configured with thermal isolation against the region of the rectification column containing the separating internals.

13. A process as claimed in claim 1, wherein the at least one chimney tray, from which the top condensate formed is removed from the rectification column, and its at least one chimney, have a double-walled configuration consisting of a higher and a lower wall.

14. A process as claimed in claim 13, wherein trace heating is mounted on the upper surface of the lower of the two walls.

* * * * *